United States Patent
DeLaet

(10) Patent No.: US 9,586,832 B2
(45) Date of Patent: Mar. 7, 2017

(54) METHOD FOR DESTRUCTION OF HALONS

(71) Applicant: Dru L. DeLaet, St. Louis, MO (US)

(72) Inventor: Dru L. DeLaet, St. Louis, MO (US)

( * ) Notice: Subject to any disclaimer, the term of this patent is extended or adjusted under 35 U.S.C. 154(b) by 312 days.

(21) Appl. No.: 14/218,879

(22) Filed: Mar. 18, 2014

(65) Prior Publication Data

US 2014/0341798 A1  Nov. 20, 2014

Related U.S. Application Data

(60) Provisional application No. 61/793,675, filed on Mar. 15, 2013.

(51) Int. Cl.
| | | |
|---|---|---|
| *C01D 3/10* | (2006.01) | |
| *C01D 3/04* | (2006.01) | |
| *C01D 3/02* | (2006.01) | |
| *C07C 263/00* | (2006.01) | |
| *C07C 209/12* | (2006.01) | |
| *C07C 291/10* | (2006.01) | |

(52) U.S. Cl.
CPC ............... *C01D 3/10* (2013.01); *C01D 3/02* (2013.01); *C01D 3/04* (2013.01); *C07C 209/12* (2013.01); *C07C 263/00* (2013.01); *C07C 291/10* (2013.01)

(58) Field of Classification Search
USPC ........ 423/490, 499.1–499.4, 245.1; 588/316, 588/317, 406
See application file for complete search history.

(56) References Cited

U.S. PATENT DOCUMENTS

| | | |
|---|---|---|
| 2,691,052 A | 10/1954 | Cines |
| 3,004,075 A | 10/1961 | Marcali |
| 3,523,982 A | 8/1970 | Vives |
| 4,118,494 A * | 10/1978 | Kunstmann .......... C07D 217/24  514/309 |
| 4,853,040 A | 8/1989 | Mazur et al. |
| 5,096,600 A | 3/1992 | Hoch |
| 5,110,364 A | 5/1992 | Mazur et al. |
| 5,292,942 A * | 3/1994 | Aigner ..................... A61K 8/44  554/52 |
| 5,345,031 A | 9/1994 | Schwartz et al. |
| 5,414,200 A | 5/1995 | Mouk et al. |
| 5,559,278 A | 9/1996 | Mouk et al. |
| 5,587,317 A | 12/1996 | Odom |
| 5,602,295 A | 2/1997 | Abel et al. |
| 5,678,231 A | 10/1997 | Mouk et al. |
| 5,997,825 A | 12/1999 | Satyapal et al. |
| 6,083,394 A | 7/2000 | Seech et al. |
| 6,576,122 B1 | 6/2003 | Bolsing |
| 6,649,044 B1 | 11/2003 | Bolsing |
| 2005/0027155 A1 | 2/2005 | Pooler et al. |
| 2012/0323006 A1 * | 12/2012 | Clary .................. C07D 209/10  544/363 |

OTHER PUBLICATIONS

Wang, Zerong "Comprehensive Organic Name Reactions and Reagents", 2010, pp. 1457-1459.*
Ahluwalia et al. "A Textbook of Organic Chemistry", Mar. 30, 2000, p. 456.*

* cited by examiner

*Primary Examiner* — Ngoc-Yen Nguyen

(74) *Attorney, Agent, or Firm* — Capitol City TechLaw, PLLC; Samuel P. Burkholder

(57) ABSTRACT

A method of reacting amine compounds with halons and perhalogenated compounds, resulting in the conversion of these ozone-depleting species into non-volatile salts and a variety of other amine derivatives is disclosed.

11 Claims, 5 Drawing Sheets

Test Labeling Methodology: Halon type - Amine type - test # (XXXX-XX-X)

Equipment tared masses:

| | |
|---|---|
| Entire Bomb: | 3362.0 g |
| w/ quick release adaptor: | 3386.1 g |
| Filter Flask #1: | 265.0 g |
| Filter Flask #2: | 195.0 g |
| Filter Flask #3: | 337.25 g |
| Coarse Filter: | 324.45 g |
| Medium Filter: | 337.5 g |

Formula Weights:

Amines

| | | |
|---|---|---|
| ADMA 12 (dimethyl dodecyl) | 207.42 | g/mol |
| ADMA 10 (dimethyl decyl) | 178.42 | g/mol |
| ADMA 16 | 263.42 | g/mol |

Halon

| | | |
|---|---|---|
| 1211 (CF$_2$ClBr) | 165.37 | g/mol |
| 1301 (CF$_3$Br) | 148.88 | g/mol |

Monoquats

| | | |
|---|---|---|
| ADMA 12 / 1211 | 372.7 | g/mol |
| ADMA 12 / 1301 | 356.4 | g/mol |
| ADMA 10 / 1301 | 327.3 | g/mol |
| ADMA 16 / 1301 | 412.3 | g/mol |

Diquats

| | | |
|---|---|---|
| ADMA 12 / 1211 | 580.2 | g/mol |
| ADMA 12 / 1301 | 563.7 | g/mol |
| ADMA 10 / 1301 | 505.72 | g/mol |
| ADMA 16 / 1301 | 675.72 | g/mol |

| Rxn # | Time (hrs) | Temp C | Molar ratio | % yield (basis) | % yield (basis) |
|---|---|---|---|---|---|
| 1211-12-6 | 24 | 90 | 10.62 | 32.51 | 20.89 |
| 1211-12-7 | 48 | 89 | 21.79 | 61.98 | 39.81 |
| 1301-10-1 | 48 | 100 | 8.33 | 0.00 | 0.00 |
| 1211-12-4 | 48 | 100 | 7.60 | 116.00 | 74.51 |
| 1211-12-1 | 48 | 110 | 1.03 | 32.40 | 113.18 |
| 1211-12-2 | 48 | 110 | 1.86 | 79.37 | 153.75 |
| 1211-12-3 | 48 | 111 | 4.20 | 87.66 | 56.31 |
| 1301-10-2 | 48 | 120 | 1.00 | 1.70 | 2.19 |
| 1301-12-1 | 48 | 120 | 20.22 | 6.94 | 10.98 |
| 1301-16-1 | 48 | 120 | 16.26 | 12.45 | 7.60 |
| 1301-10-4 | 48 | 120 | 19.82 | 12.87 | 8.33 |
| 1301-10-3 | 48 | 140 | 1.01 | 40.74 | 52.35 |
| 1301-10-5 | 72 | 120 | 16.19 | 0.22 | 0.14 |
| 1301-12-2 | 72 | 120 | 10.00 | 5.40 | 3.42 |
| 1301-12-3 | 72 | 130 | 10.24 | 10.58 | 6.69 |
| 1211-12-5 | 96 | 90 | 11.48 | 62.49 | 40.14 |
| 1211-12-7 | 48 | 89 | 21.79 | 61.98 | 39.81 |
| 1211-12-6 | 24 | 90 | 10.62 | 32.51 | 20.89 |
| 1211-12-5 | 96 | 90 | 11.48 | 62.49 | 40.14 |
| 1211-12-4 | 48 | 100 | 7.60 | 116.00 | 74.51 |
| 1211-12-1 | 48 | 110 | 1.03 | 32.40 | 113.18 |
| 1211-12-2 | 48 | 110 | 1.86 | 79.37 | 153.75 |
| 1211-12-3 | 48 | 111 | 4.20 | 87.66 | 56.31 |
| 1301-10-1 | 48 | 100 | 8.33 | 0.00 | 0.00 |
| 1301-10-2 | 48 | 120 | 1.00 | 1.70 | 2.19 |
| 1301-16-1 | 48 | 120 | 20.22 | 6.94 | 10.98 |
| 1301-10-4 | 48 | 120 | 16.26 | 12.45 | 7.60 |
| 1301-12-1 | 48 | 120 | 19.82 | 12.87 | 8.33 |
| 1301-10-5 | 72 | 120 | 16.19 | 0.22 | 0.14 |
| 1301-12-2 | 72 | 120 | 10.00 | 5.40 | 3.42 |
| 1301-12-3 | 72 | 130 | 10.24 | 10.58 | 6.69 |
| 1301-10-3 | 48 | 140 | 1.01 | 40.74 | 52.35 |

Figure 2

METHOD FOR DESTRUCTION OF HALONS

RELATED APPLICATIONS

The present application claims benefit from earlier filed U.S. Provisional Application No. 61/793,675, filed Mar. 15, 2013, which is incorporated by reference in its entirety for all purposes.

BACKGROUND

Field of the Invention

This application is generally directed to halons and more particularly, to the use of nitrogen-containing compounds in preparing nonvolatile derivatives of halons and other perhalogenated, ozone-depleting compounds.

Discussion of the Related Art

Halons are generally defined as perhalogenated alkanes, usually containing at least one bromine, while another well-known class of perhalogenated alkanes, freons, contain at least one fluorine, that are often used, among other things, as fire suppressing agents. Yet, because these compounds also damage stratospheric ozone, many have been phased out, while others are in the process of being eliminated altogether. As a result, there are stockpiles of these compounds slated for destruction, which currently occurs by incineration. There have been a limited number of other synthetic processes to convert some halons and freons into various nonvolatiles.

In one of these processes halons react in the gas phase via reductive coupling with methane at elevated temperatures, and halon 1301 ($CBrF_3$) is converted into trifluoromethane, ethylene and HBr; halon 1211 ($CBrClF_2$) is converted into difluoroethane, HCl and HBr. However, this process is run in capital intensive equipment under high purity and extreme conditions.

The reaction of amines with alkylhalides by an SN-2, bimolecular substitution mechanism, has been utilized to prepare a variety of amines and quaternary ammonium compounds. For example,

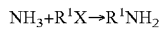

$NH_3 + R^1X \rightarrow R^1NH_2$                              1.

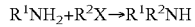

$R^1NH_2 + R^2X \rightarrow R^1R^2NH$                          2.

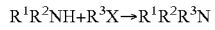

$R^1R^2NH + R^3X \rightarrow R^1R^2R^3N$                       3.

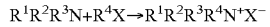

$R^1R^2R^3N + R^4X \rightarrow R^1R^2R^3R^4N^+X^-$             4.

The reaction of amines with halons (perhalogenated alkyls), however, does not easily yield quaternary ammonium compounds due to the instability of the electrophilic, halogenated alkyl byproduct. The resulting alkyl group is predicted to attach to the nitrogen atom, which is then positively charged. However, in the case of halons, the alkyl group is so electrophilic, that it is not stable with this charge. The process does include the initial bimolecular substitution reaction which eliminates either $Br^-$ or $Cl^-$.

SUMMARY OF THE INVENTION

The present application is directed to, and discloses a method of converting halogen-containing compounds by providing a halogen-containing compound, an amine-containing compound, and an alkali metal-containing compound. These three compounds are then contacted together to form a mixture, and heated to a first temperature to drive the reaction. The method further includes cooling the mixture to room temperature, and isolating the products.

Isocyanide compounds are made by a method taught herein. The method includes providing a halogen-containing compound having at least one carbon, $C^1$, providing a primary amine compound having an alkyl group, R, contacting the halogen-containing compound, and the primary amine compound together to form a mixture, heating the mixture to a first temperature, cooling the mixture to room temperature, and isolating the isocyanide compound.

The reaction of a variety of certain amines with halons produces different amines and may also produce halide salts. When the amines are tertiary amines having 3 alkyl groups attached, the amine can be utilized as a catalyst to convert the halon into non-volatile salts such as NaBr, NaF and NaCl. When the amine is a secondary amine having 2 alkyl groups and one hydrogen, a haloamine is formed. When the amine is primary, the nitrogen compound formed is an alkyl-isocyanide, $C^1NR$, where the $C^1$ carbon originated as the carbon from the halon, and the alkyl group R was the original amine alkyl chain.

The processes described herein can be run in aqueous solution, in relatively simple pressure vessels and under mild thermal conditions. Since fragments of the perhalogenated compound undergo substantial substitution the resulting compounds which contain the halogen fragments tend not to be ozone depleting.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 2 tabulates conditions and yields for various halon-amine reactions;

DETAILED DESCRIPTION

Figure 1:
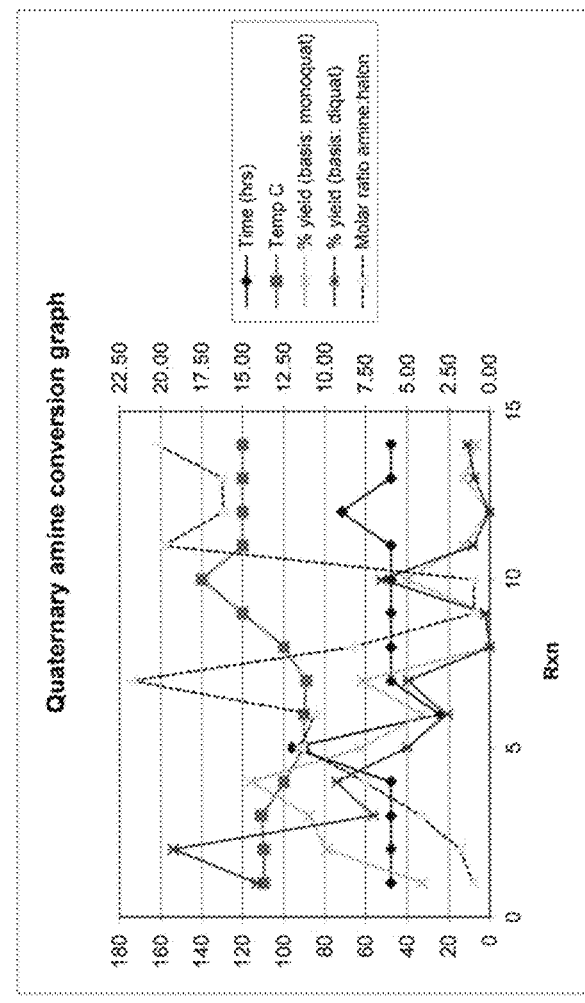
FIG. 1 tabulates conditions and yields for various halon-amine reactions and illustrates the quaternary amine conversion in a graphical form.

A method of converting halogen-containing compounds by providing a halogen-containing compound, an amine-containing compound, and an alkali metal-containing compound, contacting the halogen-containing compound, the amine-containing compound, and the alkali metal-containing compound together to form a mixture, and heating the mixture to a first temperature is disclosed by the present application. The method further includes cooling the mixture to room temperature, and isolating the products.

For the disclosed method the halogen-containing compound can include at least one compound selected from the group consisting of perhalogenated alkyls, halons, and freons. The amine-containing compound can include at least one compound selected from the group consisting of primary amines, secondary amines and tertiary amines, and the alkali metal-containing compound can include at least one compound selected from the group consisting of lithium hydroxide, sodium hydroxide and potassium hydroxide.

In some embodiments of the method, the amine-containing compound can be selected from the group consisting of amines having at least one alkyl moiety having from eight to twenty carbons.

For this method, the products include, among other compounds, alkali metal salts composed of the halogens from the halogen-containing compound and the alkali metal from the alkali metal-containing compound. These alkali metal salts can comprise sodium fluoride, sodium chloride, and sodium bromide.

Also disclosed herein is a method to make isocyanide compounds by providing a halogen-containing compound having at least one carbon, $C^1$, providing a primary amine compound having an alkyl group, R, contacting the halogen-containing compound, and the primary amine compound together to form a mixture, heating the mixture to a first temperature, cooling the mixture to room temperature, and isolating the products containing an isocyanide compound.

In the disclosed method to make isocyanides, the halogen-containing compound can include at least one compound selected from the group consisting of perhalogenated alkyls, halons, and freons. The primary amine can be selected from the group consisting of primary amines with alkyl groups containing from one to 20 carbons, with some particularly identified primary amines including methylamine, ethylamine, n-propylamine, isopropylamine, n-butylamine, iso-butylamine, n-pentylamine, iso-pentylamine, n-hexylamine and iso-hexylamine, for instance.

The isocyanide compound made by the presently disclosed method can be $C^1NR$, where the carbon, $C^1$, is derived from the halogen-containing compound and the alkyl group, R, is derived from the primary amine compound.

Additionally disclosed here, and as a representative reaction, the following is given as an example. $R^1$ and $R^2$ are methyl groups. $R^3$ is a tetradecyl group, and $R^4X$ is Halon 1211, ($CBrClF_2$). X represents bromine, as it will be the initial leaving group.

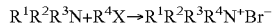

The resulting $R^4$ fragment being $—CClF_2$ is extremely electrophilic and causes the cation to be unstable, and thus in the presence of a base, the initial amine is regenerated, and the fragment continues to react to form the halide salts. In the case of halon 1301, the resulting fragment, $—CF_3$ reacts to extract a hydrogen to produce the stable gas, trifluoromethane, $HCF_3$. In aqueous-basic media the result is production of only two products the bromide salt and trifluoromethane. In this case the salt isolation may be simple while separation of $HCF_3$ from unreacted halon 1301 requires more elaborate methods such as gas selective membrane separation or a pressure/temperature "distillation" type approach.

When the amine is a secondary amine having 2 alkyl groups and one hydrogen, a chloroamine is formed. In the following example, $R^1$ and $R^2$ are ethyl groups, and $R^3X$ is again Halon 1211 ($CBrClF_2$).

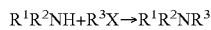

The alkyl group that has been substituted onto the nitrogen is no longer the $CClF_2$ fragment but continues the substitution process to produce the product:

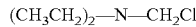

When the amine is primary, the nitrogen compound formed is an alkyl-isocyanide, $C_1NR$, where the $C_1$ carbon originated as the carbon from the halon, and the alkyl group R was the original amine alkyl chain. In this example ethyl amine is used. If ammonia is used, the small amount of products isolated are ammonium halides.

As used herein, the term "halon" refers to perhalogenated alkanes (haloalkanes, halogenoalkanes) comprising at least one bromine substituent. Accordingly, halons are represented herein using the generic formula $R_XBr$, where $R_X$ is a perhaloalkyl group. Halons are often referred to as "Halon XYZW," where X is the number of carbon atoms, Y is the number of fluorine atoms, Z is the number of chlorine atoms, and W is the number of bromine atoms. Examples of halons include Halon 1211 ($CF_2ClBr$, difluorochlorobromomethane) and Halon 1301 ($CF_3Br$, trifluorobromomethane). Other suitable halons include Halon 2402 ($C_2F_4Br_2$, 1,1,2,2-tetrafluoro-1,2-dibromoethane). Given the nature of the SN-2 reaction other chlorofluorocarbons may also be used if conditions are altered.

Because halons have been relatively high-cost materials, there was formerly little interest in their uses as synthetic intermediates. Their current status as undesirable compounds however, coupled with their availability in stockpiles, opens up their use in synthesis. Moreover, halons are multifunctional, energetic compounds, properties that contribute to their synthetic utility.

Some embodiments provide a quaternary ammonium salts of formula I:

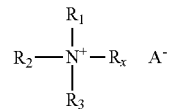

Formula I wherein $R_1$, $R_2$, and $R_3$ are independently selected from the group consisting of $C_1$-$C_{20}$ alkyl, aryl, and aralkyl; RX is $C_1$-$C_{20}$ perhaloalkyl; and A– is any suitable anion. As used herein, the term "alkyl" includes straight-chain, branched, and cyclic alkyl groups, and combinations thereof. The term "aralkyl" includes substituents comprising aryl substituted alkyl group such as benzyl and phenethyl. Those skilled in the art will understand that in some embodiments, the anion $A^-$ is a monoanion, a dianion, a trianion, or a polyanion. In other situations, at least two of $R_1$, $R_2$, and $R_3$ are independently lower alkyls, more preferably, methyl and/or sometimes ethyl. Another scenario occurs when at least two of $R_1$, $R_2$, and $R_3$ groups are n-alkyls from about $C_8$ to about $C_{20}$. In some preferred embodiments, $R_X$ is selected from the group, consisting of $—CF_2Cl$, $—CF_3$ or more commonly $—H$. Other times, $A^-$ is bromide. Where $R_1$ and $R_2$ are methyl, $R_3$ is n-alkyl from about $C_8$ to about $C_{20}$, and $R_X$ is selected from the group consisting of $—CF_2Cl$ and $—CF_3$.

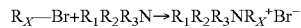 SCHEME A $R_1$, $R_2$, and $R_3$, and $R_X$ are defined above. Embodiments of the reaction are performed in the gas phase, a condensed phase or in a reaction mixture comprising both gas and condensed phases. Some embodiments use one or more suitable solvents, such as ethyl acetate, methyl ethyl ketone or water. In others, at least a portion of the reaction is performed neat. This reaction can be performed in a batch reactor or a flow reactor.

According to various embodiments of the present disclosure, reaction temperatures are from ambient to the boiling temperature of at least one of the reactants, such as, the tertiary amine. In some embodiments, the reaction temperature is greater than about 100° C., greater than about 125° C., greater than about 150° C., greater than about 165° C., greater than about 180° C. or greater than about 200° C. For example, in other embodiments, the reaction temperature is higher than the boiling point of at least one of the reactants. Some embodiments use a plurality of reaction temperatures and/or temperature gradients.

The various reactions of the present disclosure can produce a variety of products such as halogen salts, other amine derivatives and, potentially, unique quaternary ammonium compounds. The salts may be useful in applications ranging from strengthening teeth and glass etching (for fluorides), nutrition, manufacturing photographic chemicals and flame retardants (for bromides and chlorides), or for the recovery of the halogen itself. The amines and quaternary compounds have shown potential as surfactants, biocides, and/or phase transfer agents.

Embodiments of the reaction are performed at pressure of from about 1 torr to about 10 atm. In some preferred embodiments, the reaction is performed at ambient pressure. Those skilled in the art will understand that, in some embodiments, the reaction temperatures and pressures are related, for example, with reaction rate increasing with temperature and/or pressure.

EXPERIMENTAL

General Procedure

The following experiments were performed using a 250-mL or 500-mL (Autoclave Engineers) bomb reactor. Each was equipped with a pressure gauge and a thermocouple. Temperature control was provided using a heating tape wrapped around the reactor and a temperature controller. The reactor was charged with the appropriate tertiary amine and closed. The desired quantity of halon was then added through a gas inlet and the bomb reactor sealed.

Numerous experiments with variations in reaction conditions and starting materials have been performed. The majority of amines used were N,N-dimethyl fatty amines and those given in the following Examples. Halons tested were Halon 1211 or Halon 1301. Recrystallizations were performed using ethylacetate as a recrystallizing solvent.

Figure 3:
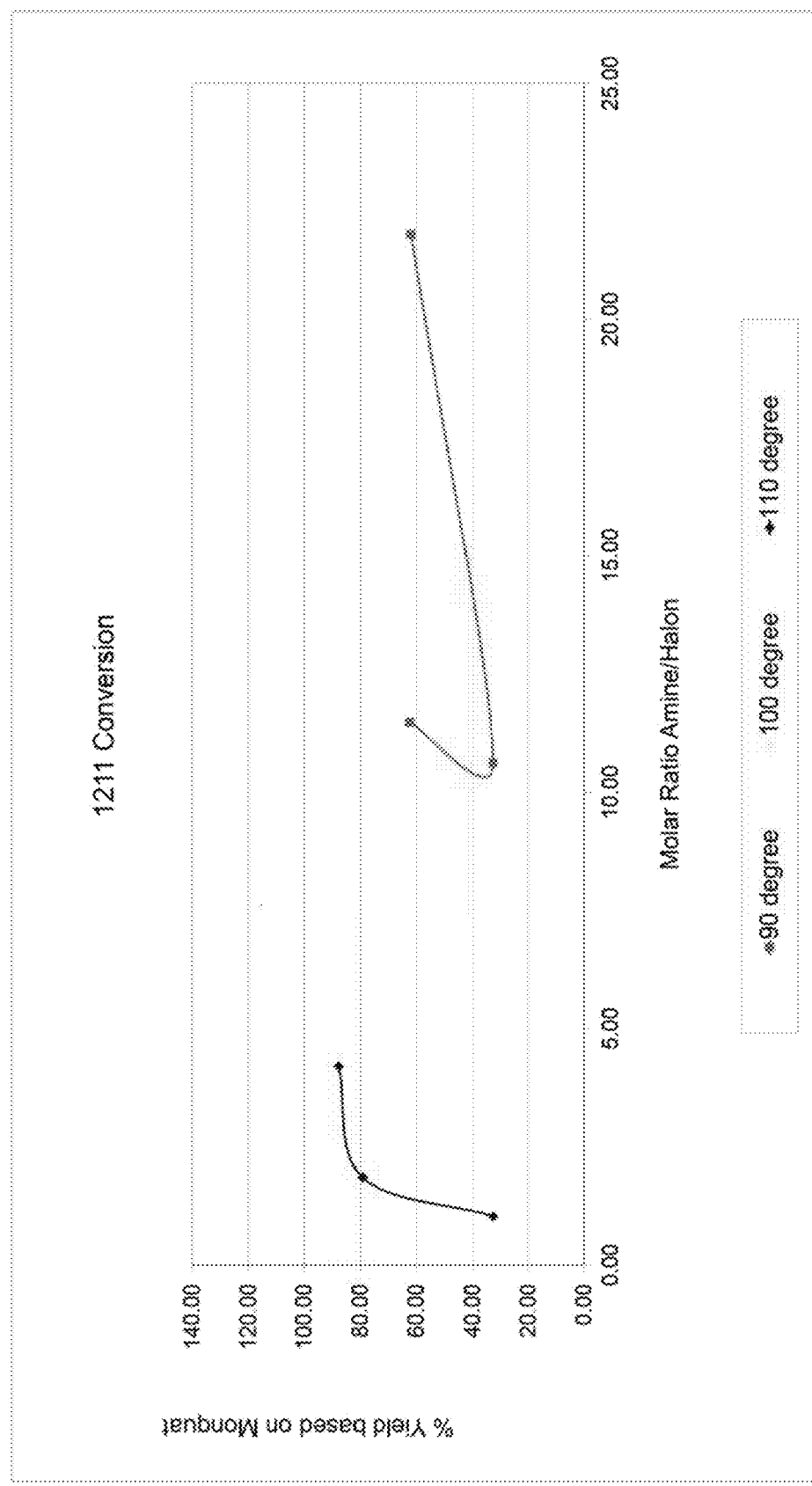
FIG. 3 illustrates the 1211 halon reaction results in a graphical form.
Figure 4:
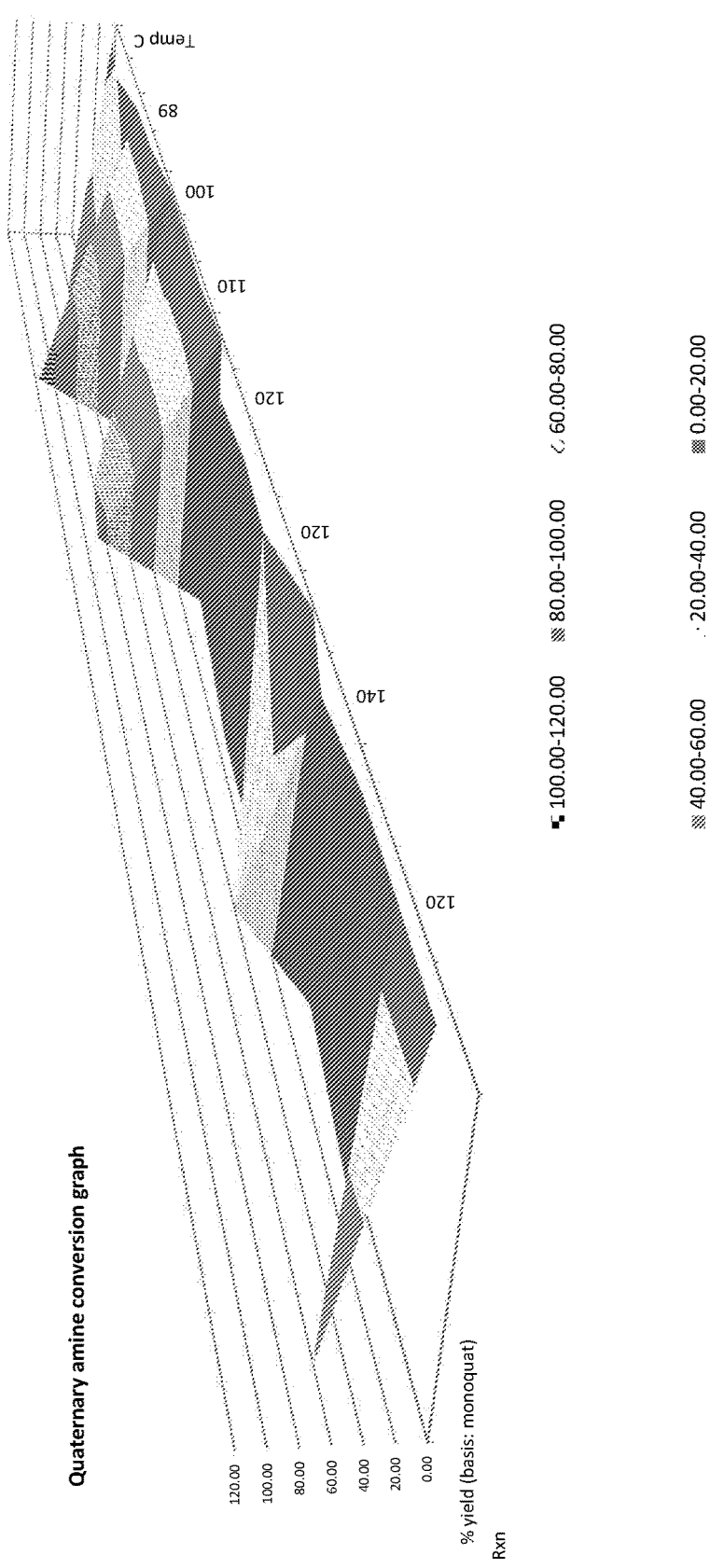
FIG. 4 illustrates the quaternary amine conversion results in a graphical form.
Figure 5:
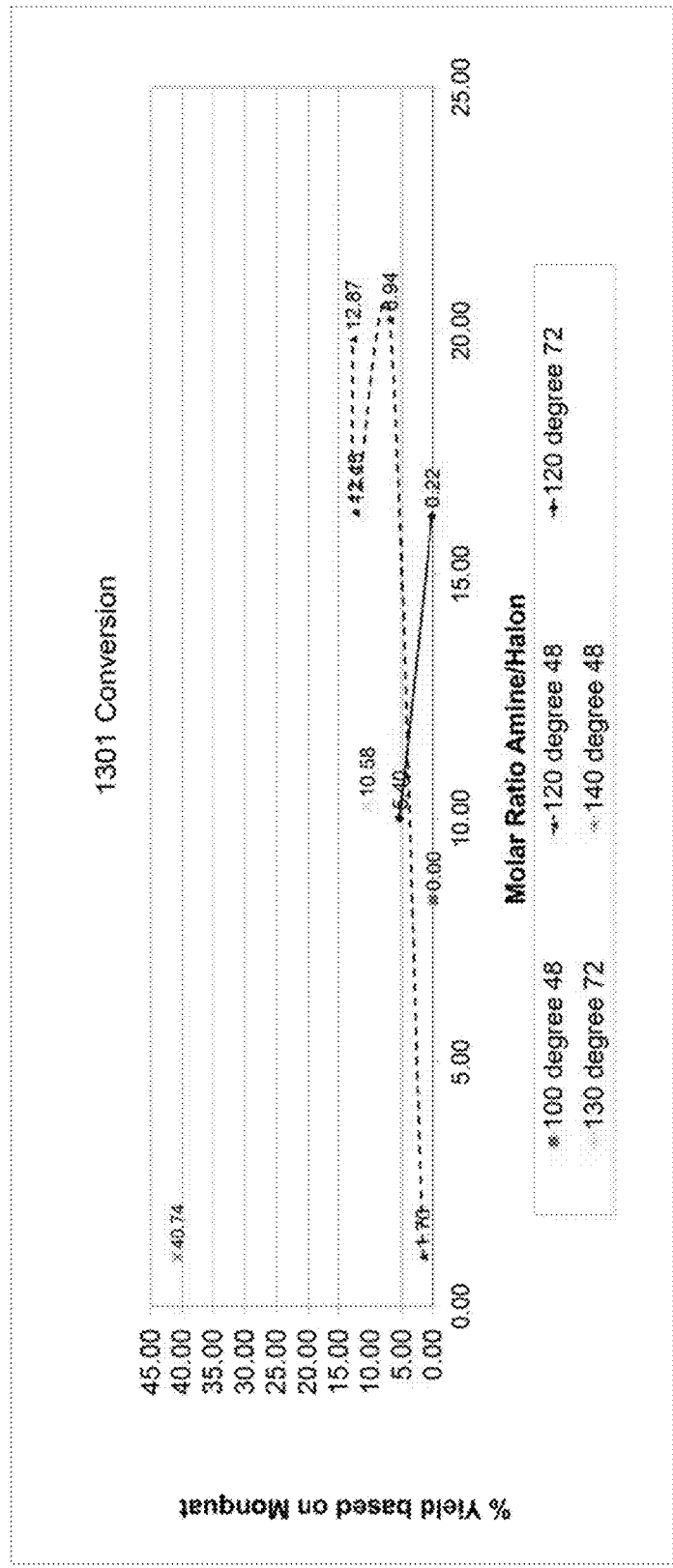
FIG. 5 illustrates the 1301 halon reaction results in a graphical form.

Various of the experimental results are tabulated in Tables 1 and 2 herein. These bomb reactor experiments are labeled "Halon type-Amine type-test number" in the attached data tables. The halons were either halon 1211 ($CF_2ClBr$) or halon 1301 ($CF_3Br$), and the amines were one of ADMA 10, 12 or 16. "ADMA" is a group of alkyldimethylamines composed of even-numbered carbon chains from $C_8$ to $C_{18}$, and is the trademark of the Albemarle Corporation. The reactions were run for 24, 48, 72, or 96 hours, at temperatures ranging from 90 C up to 140 C in 10 degree C. steps. The molar ratio between the amine and halon were also varied from 1:1 up to almost 22:1. The reaction yields and halon conversion rates are also presented in FIGS. 1-5.

Example 1

The Reaction of Dimethyltetradecylamine with Halon 1211

Following the same general procedure set forth above, 111.5 grams of dimethyltetradecylamine (ADMA-14) was added to the 250 mL reactor along with 100.7 grams of Halon 1211. The reactor was sealed for 24 h at 100 C. Reactor pressure reached 98 psi at the end of the 24 h period. The reactor was then vented. Off-gases were analyzed using GC/MS. The crystalline solid (82.9 grams) was washed twice with petroleum ether and evaluated by elemental analysis and Ion Chromatography. The off-gas analysis was consistent with continued reactivity of the halon fragment and consisted of a mixture of Halon 1211, chlorodifluoromethane, trifluoromethane and several other perhalogenated species; this off-gas analysis was also observed in numerous other examples. The analysis of the solid material is fully consistent with the protonated amine with a bromide anion.

Example 2

The Reaction of Dimethyltetradecylamine with Halon 1301

Following the procedure outlined above, 80 grams of the amine ADMA-14 and 33.6 grams of Halon 1301 were added to the reactor and sealed for a period of 95 h at 120 C. Ten grams of solid were isolated and analyzed. Again the product was consistent with the protonated amine with a bromide counterion.

Example 3

The Reaction of Ammonia with Halon 1211

In this example, 30% ammonium hydroxide solution (50 grams) was added to the reactor along with 35 grams of Halon 1211. The reactor was sealed for 48 h at a temperature of 90 C. The pressure was released, and the reactor's contents removed. The solution was evaporated to yield 0.2 grams of solid, identified as a mixture of ammonium fluoride, ammonium bromide and ammonium chloride in the appropriate 2/1/1 molar ratio.

Example 4

The Reaction of Diethylamine with Halon 1211

Following the same procedure as above, 30 grams of diethylamine and 68 grams of Halon 1211 were sealed in the reactor. The reactor was heated to 100 C for 48 h. Isolation of the product was performed by distillation. The liquid product had a b.p. at approximately 120 C. This pure material was analyzed using H1-NMR, C13-NMR, and elemental analysis. All were consistent with the product being diethyl-chloromethyl amine.

Example 5

The Reaction of Ethylamine with Halon 1211

In this example, the reactor was charged with 30 grams of ethylamine (70% aqueous solution) and 45 grams of Halon 1211. The reactor was sealed and heated to 100 C for 48 h. One gram of ethyl-isocyanide was isolated from the reaction mixture by distillation. Its identity was confirmed by H1-NMR and its pungent acrid odor.

Example 6

The Reaction of Dimethyltetradecylamine with Halon 1211 and Sodium Hydroxide

In this example, an aqueous sodium hydroxide phase was introduced to the reactor. The reactor was charged with 80.6 grams of 30% aqueous sodium hydroxide, 49.6 grams of ADMA-14 and 33.4 grams of Halon 1211. The reactor was sealed for 48 h at 90 C. Pressure increased to 35 psi over the 48 h period. The head space analysis demonstrated again the reactivity of the halogenated fragment with nearly the same mixture as seen in example 2. However, the product of this reaction was soluble in the aqueous layer. The amine was fully recovered. Analysis by ion chromatography of the aqueous layer showed substantial presence of fluoride, chloride and bromide—nearly 32 grams.

Example 7

The Reaction of Dimethyltetradecylamine with Halon 1211 and Sodium Hydroxide in a Stirred Reactor Following the same procedure as example 6, the reactor was charged with 82 grams of 30% aqueous sodium hydroxide, 52.2 grams of ADMA-14 and 36.9 grams of Halon 1211. The reactor was sealed for 48 h at 90 C. In this case, the reactor was stirred. The results were nearly identical to example 6. Yet, in this case, an emulsion had formed due to a small amount of quaternary ammonium acting as a surfactant in the highly agitated system. Isolation of the two phases was accomplished by the heating and evaporation of the water. The head-space gases also contained one compound in significant amount: dichloro-tetrafluoroethane.

Example 8

The Reaction of Dimethyltetradecylamine with Halon 1301 and Sodium Hydroxide without Agitation Following the same procedure as example 6, the reactor was charged with 80.2 grams of 30% aqueous sodium hydroxide, 49.8 grams of ADMA-14 and 30.7 grams of Halon 1301. The reactor was sealed for 48 h at 90 C. The reactor pressure increased to 230 psi over the 48 hour period. The reactor was depressurized and the off gasses were passed through two caustic scrubbers in series. The assay results showed a 3% conversion of Halon 1301 in which the bromine was in the aqueous phase and the fluorine was in the gas phase as trifluoromethane. The amine was recovered quantitatively. Isolation of the two phases was accomplished by separatory funnel.

Example 9

The Reaction of Dimethyltetradecylamine with Halon 1301 and Sodium Hydroxide in a Stirred Reactor Following the same procedure as example 8, the reactor was charged with 83 grams of 30% aqueous sodium hydroxide, 49.8 grams of ADMA-14 and 30.6 grams of Halon 1301. The reactor was sealed for 48 h at 90 C. In this case, unlike the previous example, the reactor's contents were stirred. The results of the reaction were nearly identical to Example 8 above but with a greatly increased yield, 91.4%. In this case an emulsion had formed which is believed to have been caused by a small amount of quaternary ammonium compound acting as a surfactant in the highly agitated system. Isolation of the phases was accomplished by centrifuge. Isolation of the phases could also be accomplished by separatory funnel at elevated temperature. The amine was recovered quantitatively. All bromine, as NaBr, was found in the aqueous phase and fluorine was found in the gas phase as trifluoromethane.

All publications, articles, papers, patents, patent publications, and other references cited herein are hereby incorporated by reference herein in their entireties for all purposes.

Although the foregoing description is directed to the preferred embodiments of the present teachings, it is noted that other variations and modifications will be apparent to those skilled in the art, and which may be made without departing from the spirit or scope of the present teachings.

The foregoing detailed description of the various embodiments of the present teachings has been provided for the purposes of illustration and description. It is not intended to be exhaustive or to limit the present teachings to the precise embodiments disclosed. Many modifications and variations will be apparent to practitioners skilled in this art. The embodiments were chosen and described in order to best explain the principles of the present teachings and their practical application, thereby enabling others skilled in the art to understand the present teachings for various embodiments and with various modifications as are suited to the particular use contemplated. It is intended that the scope of the present teachings be defined by the following claims and their equivalents.

I claim:

1. A method of converting halogen-containing compounds comprising
   providing a first compound consisting of at least one compound selected from the group consisting of perhalogenated alkyls, halons, and freons,
   providing an tertiary amine-containing compound,
   providing at least one second compound selected from the group consisting of lithium hydroxide, sodium hydroxide and potassium hydroxide,
   contacting the first compound, the amine-containing compound, and the second compound together to form a mixture,
   heating the mixture to a first temperature,
   reacting the first and second compounds in the presence of the tertiary amine-containing compound within the mixture to form a reacted mixture,
   allowing the reacted mixture to cool to room temperature, and
   isolating products from the cooled reacted mixture,
   wherein the products comprise alkali metal salts composed of the halogens from the first compound and the alkali metal from the second compound.

2. The method according to claim 1, wherein the amine-containing compound comprises at least one compound selected from the group consisting of tertiary amines having at least one alkyl moiety having from eight to twenty carbons.

3. The method according to claim 1, wherein the alkali metal salts comprise at least one member selected from the group consisting of sodium fluoride, sodium chloride, and sodium bromide.

4. A process for decomposing halogen-containing compounds comprising
   providing a tertiary amine-containing catalyst,
   providing a first compound consisting of at least one compound selected from the group consisting of alkyls, halons, and freons,
   providing a second compound comprising an alkali metal-containing compound,
   reacting the first compound with the alkali metal-containing compound in the presence of the tertiary amine-containing catalyst to form alkali metal salts composed of halogens from the first compound and alkali metal from the second compound, and recovering the tertiary amine-containing catalyst.

5. The process according to claim 4, wherein the tertiary amine-containing catalyst comprises at least one compound selected from the group consisting of tertiary amines having at least one alkyl moiety having from eight to twenty carbons.

6. The process according to claim 4, wherein the alkali metal salts comprise at least one member selected from the group consisting of sodium fluoride, sodium chloride, and sodium bromide.

7. The process according to claim 4, wherein the recovered tertiary amine-containing catalyst is re-used in the process.

8. The process according to claim 4, wherein alkali metal-containing compound is selected from the group consisting of lithium hydroxide, sodium hydroxide and potassium hydroxide.

9. A method of converting halogen-containing compounds comprising providing a first compound consisting of at least one compound selected from the group consisting of perhalogenated alkyls, halons, and freons, providing a tertiary amine-containing compound, providing an alkali metal-containing hydroxide, contacting the first compound, the tertiary amine-containing compound, and the alkali metal-containing hydroxide together to form a mixture, heating the mixture to a first temperature, reacting the first compound with the alkali metal-containing hydroxide in the presence of the tertiary amine-containing compound within the mixture to form a reacted mixture, allowing the reacted mixture to cool to room temperature, and isolating products from the cooled reacted mixture, wherein the products comprise sodium fluoride, sodium chloride, and sodium bromide.

10. The method according to claim 9, wherein the alkali metal-containing compound comprises at least one compound selected from the group consisting of lithium hydroxide, sodium hydroxide and potassium hydroxide.

11. The method according to claim 9, wherein the tertiary amine-containing compound comprises at least one compound selected from the group consisting of tertiary amines having at least one alkyl moiety having from eight to twenty carbons.

* * * * *